Figure 1A:
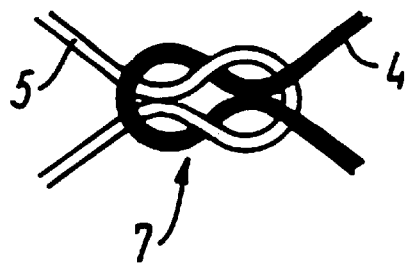

United States Patent
Kavteladze et al.

[11] Patent Number: 6,063,113
[45] Date of Patent: May 16, 2000

[54] DEVICE FOR IMPLANTATION IN A VESSEL OR HOLLOW ORGAN LUMEN

[75] Inventors: Zaza A. Kavteladze, Moscow; Alexander P Korshok, Mosckovskaya, both of Russian Federation

[73] Assignee: William Cook Europe ApS, Bjaeverskov, Denmark

[21] Appl. No.: 08/981,817

[22] PCT Filed: Jun. 11, 1996

[86] PCT No.: PCT/DK96/00254

§ 371 Date: Dec. 5, 1997

§ 102(e) Date: Dec. 5, 1997

[87] PCT Pub. No.: WO96/41589

PCT Pub. Date: Dec. 27, 1996

[30] Foreign Application Priority Data

Jun. 13, 1995 [RU] Russian Federation .............. 95109746

[51] Int. Cl.[7] ................................................. A61F 2/06
[52] U.S. Cl. ............................................ 623/1.15; 606/200
[58] Field of Search ........................ 623/1, 12; 289/1.2, 289/4

[56] References Cited

U.S. PATENT DOCUMENTS

| | | | |
|---|---|---|---|
| 2,740,185 | 4/1956 | Silver | 289/1.2 |
| 3,591,217 | 7/1971 | Melzer | 289/2 |
| 4,651,620 | 3/1987 | Lyons | 289/1.2 |
| 4,711,476 | 12/1987 | Hanson | 289/1.2 |
| 5,366,504 | 11/1994 | Andersen et al. | |
| 5,370,683 | 12/1994 | Fontaine . | |
| 5,382,259 | 1/1995 | Phelps et al. . | |
| 5,540,712 | 7/1996 | Kleshinski et al. | 606/198 |
| 5,643,339 | 7/1997 | Kavteladze et al. | 623/1 |
| 5,697,971 | 12/1997 | Fischell et al. | 623/1 |
| 5,702,418 | 12/1997 | Ravenscroft . | |
| 5,755,769 | 5/1998 | Richard et al. | 623/1 |
| 5,766,237 | 6/1998 | Cragg | 623/1 |
| 5,776,161 | 7/1998 | Globerman | 606/194 |
| 5,776,180 | 7/1998 | Goicoechea et al. | 623/1 |
| 5,782,904 | 6/1998 | White et al. | 623/1 |
| 5,782,906 | 7/1998 | Marshall et al. | 623/1 |
| 5,800,519 | 9/1998 | Sandock | 623/1 |

FOREIGN PATENT DOCUMENTS

| | | |
|---|---|---|
| 0221570 | 5/1987 | European Pat. Off. . |
| 0556850 | 8/1993 | European Pat. Off. . |
| 0622088 | 11/1994 | European Pat. Off. . |
| 9403127 | 2/1994 | WIPO . |
| 9412136 | 6/1994 | WIPO . |

*Primary Examiner*—David H. Willse
*Assistant Examiner*—Suzette J. Jackson
*Attorney, Agent, or Firm*—Richard J. Godlewski

[57] ABSTRACT

A device for implantation in a vessel or hollow organ lumen in a human or animal body, such as a self-expanding stent, a cava filter, an embolizing means or a supporting means, comprises a wire frame with a plurality of interconnected cells made of at least two separate wire sections which are intercrossing at cell junctions and form closed cells. At the cell junctions the wires are knot to form a geometrical locking of the cells so that the wire-shaped cell sides in respective cells are locked at the cell junctions when the wire frame is subjected to pressure acting radially inwards.

20 Claims, 7 Drawing Sheets

DEVICE FOR IMPLANTATION IN A VESSEL OR HOLLOW ORGAN LUMEN

The invention relates to a device for implantation in a vessel or hollow organ lumen in a human or animal body, such as a self-expanding stent, a cava filter, an embolizing means or a supporting means, the device comprising a wire frame with a plurality of interconnected cells made of at least two separate wire sections which are intercrossing at cell junctions and form closed cells.

Medical implantation devices to which the invention pertains have found wide-spread use in percutaneous vascular and cardiac surgery and comprise in particular stents, intravenous filter devices for the capture of thrombi in major veins such as the lower caval vein and occlusion devices for permanent or temporary obturation of a vessel lumen or permanent occlusion of defects in vascular walls such as an ASD in the atrial septum, a PDA defect or other defects in vascular walls such as the inlet of an exfoliative aneurism of the aorta or a puncture hole in connection with angiographic investigation.

A stent is a device that can be placed within the lumen, or interior space, of a tubular structure for supporting and assuring patency of a lumen, viz. re-opening of or keeping the lumen open. Stents are used, for example, for holding blood vessels open or for back tacking intimal flaps inside vessels after angioplasty. More generally, however, stents can be used inside the lumina of any physiological conduit including arteries, veins, vessels, the bilary tree, the urinary tract, the alimentary tract, the tracheobronchial tree, the genitourinary system, and the cerebral aqueduct.

The above mentioned device in the form of a self-expanding stent is known from WO94/03127 where the cells have a mainly square shape in a developed view. The wire sections are twisted one turn about each other about a twist axis extending in the longitudinal direction of the tubular frame body. When a stent with such cell junctions is subjected to a radial inwards pressure in a local area the cell junctions act as hinge joints allowing the cells in the pressure affected area to collapse at a relatively low pressure loading. This drawback may disqualify use of the stent in a body vessel positioned in vicinity of rigid structures such as a bone, because the pressure from such structure may cause a significant reduction of the vessel lumen due to collapsed cells.

A number of other implantation devices are known. EP-B-0 221 570 describes an expandable graft having a frame body made of a plurality of wires extending helically in opposite directions through the body. The wires may in one embodiment be woven in a criss-crossed pattern, but this does not provide cells of well-defined size br shape, because the wires may easily slide at the wire intersections. In another embodiment this is prevented by fixing the wires at the intersections by soldering, welding, or gluing. Such fixing involves the rather serious drawback that the resulting device comprises additional substances which may cause tissue reactions. A similar drawback is present in the vascular stents known from e.g. US-A-5 370 683, and EP-A-0 556 850 where the wire sections are joined by a ring of suture material at the cell junctions. In addition this latter embodiment is very time-consuming to manufacture. WO94/12136 describes a stent for use in the esophagus. The stent is formed by very loosely interknitted loops of filament so that each loop is free to slide with respect of the other loops. The sliding allows the stent to follow movements of the esophagus without axial movement of the stent, when the person is swallowing.

EP-A-0 622 088 shows coupling of two or more Z-shaped stents in an end-to-end configuration by providing the stents with eyes, at the stent ends, hooking the eyes into one another and closing the eyes by soldering, which also introduces additional substances.

An object of the present invention is to provide a device for implantation having cells which are rigidly interlocked and have a relatively large rigidity to local radial compression without requiring use of additional substances for locking the wires at the cell junctions.

With a view to this the device according to the invention is in a first aspect characterized in that at the cell junctions the wires themselves are knotted into geometrically locked cells junctions so that the wire-shaped cell sides in respective cells are locked at the cell junctions when the wire frame is subjected to pressure acting radially inwards.

The knotted wires at the cell junctions provide the desired locking by using only wire material so that the previously used solder, glue or suture may be dispensed with. This greatly improves the biological compatibility of the device and reduces risks of undesirable tissue reactions. The locking of the cell sides at the cell junctions make the individual cell a rigidly closed functional element which largely maintains its stiffness to radial compression in a local area because the geometrical locking prevents deflection of a cell side in being transferred to the subsequent cells in the longitudinal direction of the frame. When compared to the first mentioned prior art stent, the geometrical locking naturally raises the stress level in wire material constituting the individual cell sides, however the stress levels will not be higher than in the prior art stents with soldered junctions and comparable wire dimensions. It is also an advantage that the wire sections due to the knot cell junctions extend through the surface of the frame in a certain pattern, which depends on the chosen type of knots or combination of knots in the frame, because the continuous run of the wire sections provide the frame with a more even distribution or variation of stiffnesses than obtainable with several frame portions joined by sutures or other rings. In many applications such slow variation of the frame properties is advantageous in order to avoid or reduce vessel trauma or damage, in particular if the device is intended for long-term positioning in a vessel.

In a preferred embodiment the wire frame, in a developed view, includes rhomboid cells each having four cell sides and four cell junctions positioned at the apices of the cell. The rhomboid cell shape is particularly advantageous in that the tubular frame obtains a comparatively large radial stiffness in relation to the amount of wire material used, which during introduction of the frame in a radially compressed state promotes usage of a small diameter introducer sheet, allowing true percutaneous techniques with a sheet with an outer measure of 14 or 16 French. Very varied frame shapes with irregular geometries, such as tubular portions combined with cone-shaped portions may be built with rhomboid cells. A high rigidity is obtained by the geometrical locking of each cell at the four junctions, and due to the fact that the geometrically locked junctions are produced at the twining of the wire sections into the frame with knots, supplementary manufacturing steps are avoided which is favourable when the frame has a complicated geometry.

In another embodiment the wire frame, in a developed view, includes square cells each having four cell sides and four cell junctions. The square cells may be useful in frame sections having an even diameter, and they provide the frame with a large radial stiffness.

In a further embodiment the wire frame, in a developed view, includes polygonal cells each having more that four cell sides and a corresponding number of cell junctions. Such cells may, as an example be useful in cone-shaped surfaces or in areas providing transition between two regularly shaped frame sections or in areas where the type of cells are changing. Other cell shapes, such as triangular or circular are also possible.

With respect to the knot types it is for many of the frame geometries preferred that the wire frame includes cell junctions where two wire sections are loop-shaped, and that the two cell sides carrying the loop on one of the wire sections pass through the loop of the other wire section and vice versa, whereby said junctions preferably are square knot-like. This type of knot provides secure locking and is particularly useful in connection with rhomboid or diamond shaped cells because the knot returns the wire section to the same side as that which it approached the knot leading to a zigzagging run of each wire section along the length of the wire frame. The embodiment may apart from square knot (reef-knot) types also be used to make the less preferred granny knot types of knot.

Another embodiment includes a knot specially designed to lock a cell side of adjustable length between a pair of cell junctions. In this embodiment the wire frame includes pairs of cell junctions where the one wire section is looped once over and under the other wire section, and vice versa at each cell junction, and between the junctions in a pair the wire sections are twisted at least one turn about each other. In this type of knot the wire section exits to the same side of the pair of cell junctions as that which it approached leading to a kind of wavy run of each wire section.

In some types of wire frames it is desired to have each wire section run in a stepped helical configuration through a frame portion or it is desired to shift a zigzagging or a wavy run of a wire through one row of cells to a run through another row of cells. For that purpose the wire frame may include cell junctions where two wire sections are twisted one turn about each other about a twist axis extending in a first direction and at least one turn about each other about a second twist axis extending at an angle, preferably at approximately 90° to said first direction. This type of knot further provides secure locking of the two wire sections in two mutually angled directions which results in a geometrically very stable cell junction. If the cell junction is at a position of changing frame geometry said angle may e.g. be 20°, 30°, 45° or 60°, but for many applications an angle in the range of 85–95° would be preferable.

The latter embodiment may preferably be tailored for stents in that the wire frame includes a tubular portion with a mainly even diameter, and that said first direction extends approximately in the circumferential direction of said tubular portion and said second twist axis extends approximately in the longitudinal direction of said tubular portion.

In another embodiment the wire frame having rhomboid cells includes a tubular portion with cell junctions where two wire sections are twisted at least one turn about each other about a twist axis extending approximately in the circumferential direction of said tubular portion. These junctions are useable in connection with cells of rhomboid shape. The circumferential extent of the twist axis prevents the cells from opening under radial load.

According to a second aspect the device according to the invention is characterized in that the tubular wire frame, in a developed view, includes rhomboid cells each having four cell sides and four cell junctions positioned at the apices of the cell, that at each cell junction the wires are twisted one turn around each other about a twist axis directed in the circumferential direction of the tubular frame, said wires being mutually diverging away from the twist axis, so that the wire-shaped cell sides in respective cells are geometrically locked at the cell junctions when the wire frame is subjected to pressure acting radially inwards. The locking of the cell sides at the cell junctions is with this configuration obtained without use af additional substances.

Figure 1B:
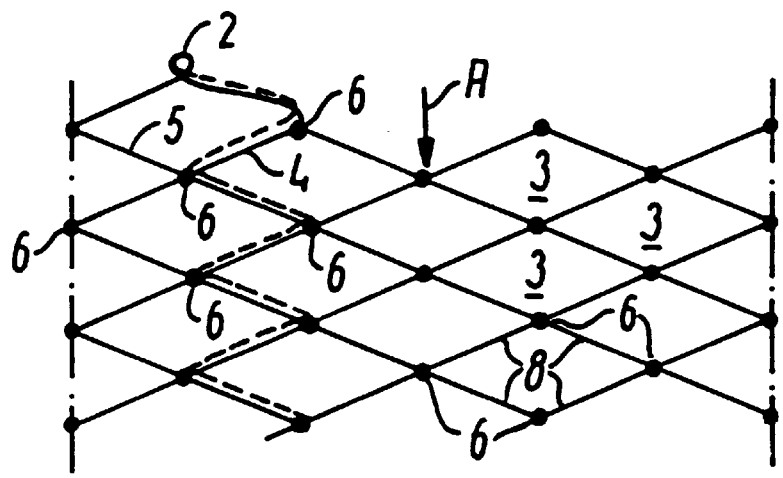
Figure 1C:
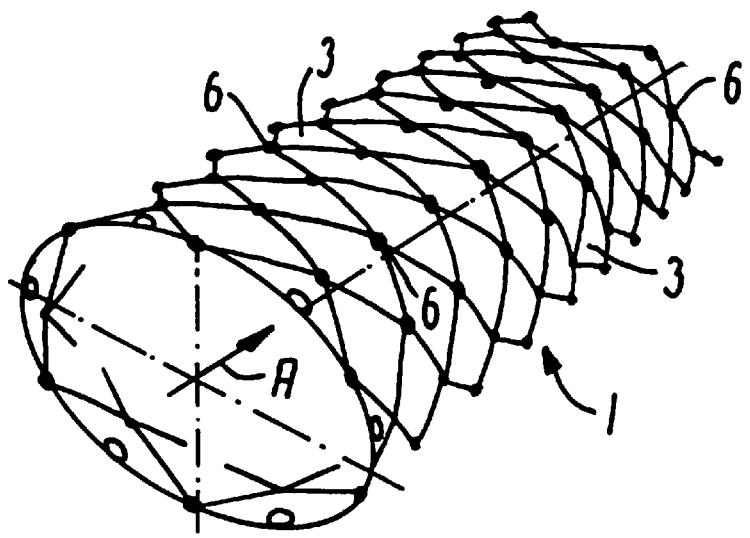
Figure 2A:
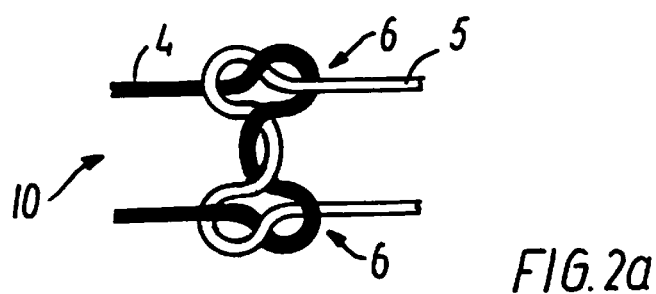
Figure 2B:
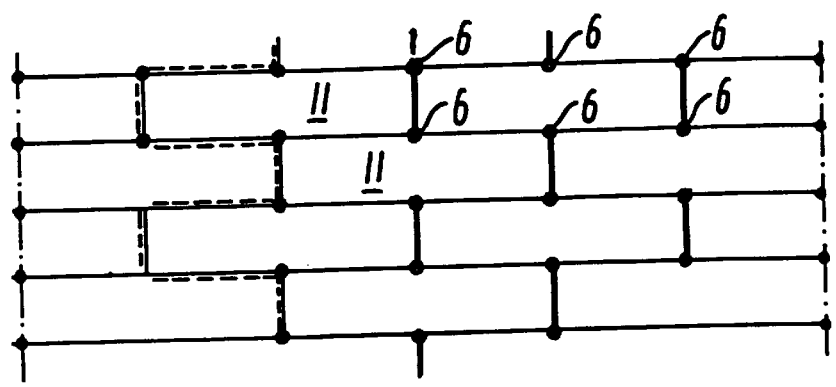
Figure 2C:
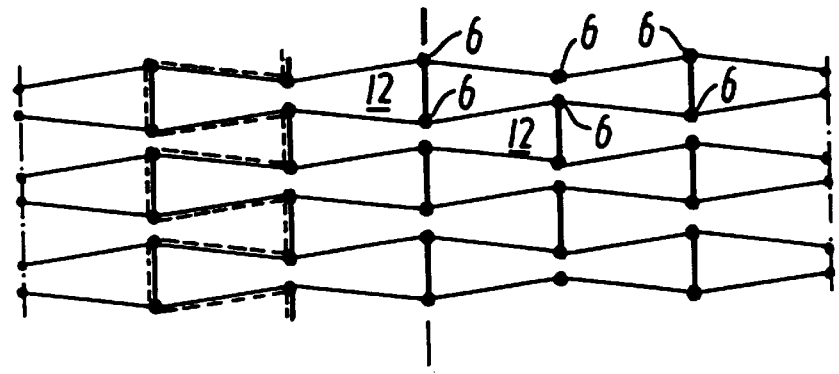
Figure 2D:
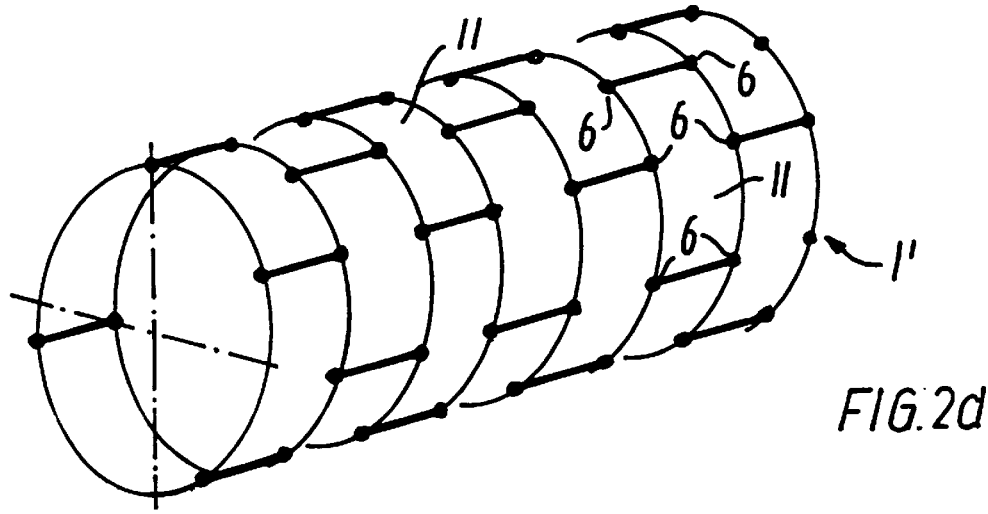
Figure 3A:
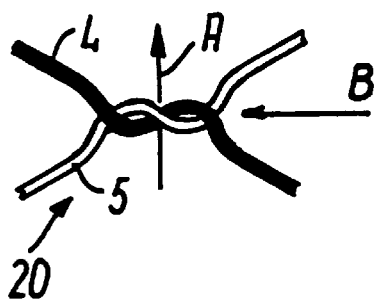
Figure 3B:
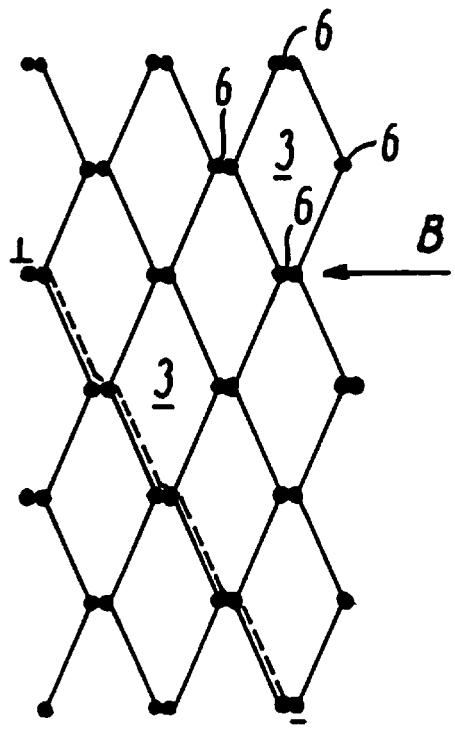
Figure 3C:
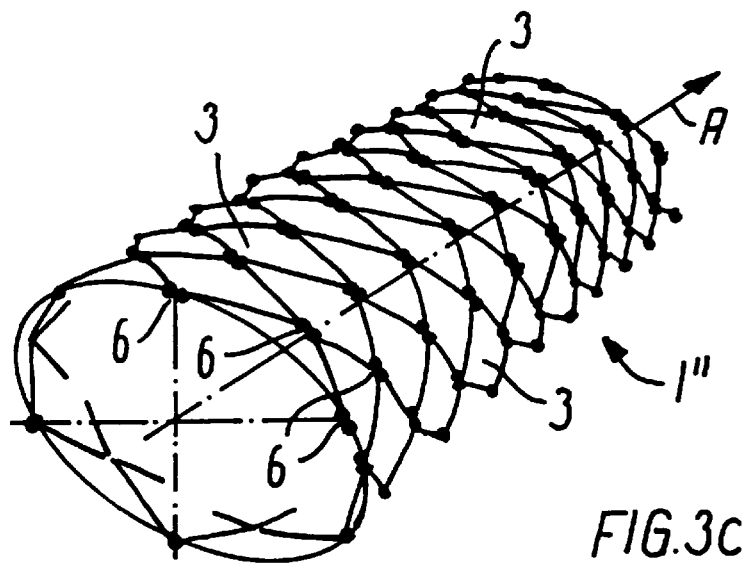
Figure 4:
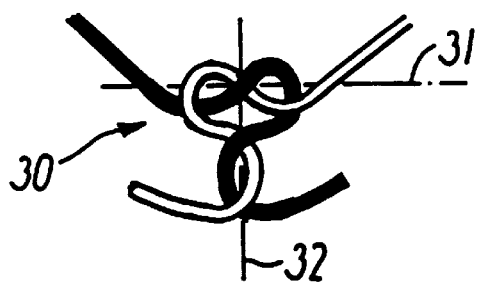

Examples of embodiments according to the invention will be, described in further detail in the following with reference to the very schematic drawings, in which FIG. 1a shows a first type of a knot at a cell junction in a wire frame of a device according to the invention, FIGS. 1b and 1c show in a developed view a section of a frame wall in an embodiment with rhomboid cells and part of a stent having such a frame wall, respectively, FIG. 2a shows a second type of a knot at a pair of cell junctions in a wire frame of a device according to the invention, FIGS. 2b, 2c and 2d show in a developed view a section of two different frame walls in embodiments with square cells and polygonal cells and part of a stent having a frame wall of the type shown in FIG. 2b, respectively, FIG. 3a shows a third type of a cell junction in a wire frame of a device according to the second aspect of the invention, FIGS. 3b and 3c show in a developed view a section of a frame wall in an embodiment with rhomboid cells and part of a stent having such a frame wall of the type shown in FIG. 3b, respectively, FIG. 4 shows a fourth type of a knot at a cell junction in a wire frame of a device according to the invention, and FIGS. 5a–5e, 6A–6E and 7a–7c show different embodiments of devices according to the invention.

In FIGS. 1b and 1c is shown part of a wire frame generally designated 1. The wire frame is made of several wire sections or filament sections which on a mandrel are bent and knotted into the desired frame shape. The mandrel includes in a well known manner a plurality of guide pins positioned on the mandrel in dependency upon the desired shape of the cells in the frame. In FIG. 1b is shown the first guide pin 2 for a row of cells 3 extending in the longitudinal direction of the frame 1. The two wire sections 4, 5 used for the row of cells preferably consists of a single length of wire which is looped around the first guide pin 2 so that the two sections extend from the pin. The run of one of the wire sections in a zigzagging course in the longitudinal direction A of the frame is in FIG. 1b indicated by a broken line following said wire section 4. Similar lengths of wire or filament is looped around similar first guide pins, not shown, pertaining to the other longitudinal rows of cells in the wire frame to be manufactured. At cell junctions 6 marked by black dots in the figures the two wire sections extending to the junction are manipulated to form the knot of the desired type and then bend towards their respective next junction. The cells are preferably made one circumferential row after the other by bending successive pairs of wire sections towards the next cell junction, making the knot and repeating these steps with the circumferentially next pairs of wire sections until a complete circumferential row of cells has been made, and the next circumferential row of cells is made in a similar manner etcetera, until the wire frame is completed.

The first type of knot shown in FIG. 1a is a square or reef-knot 7 which may be made by twisting the two wire sections 4, 5 one turn around each other, reversing the direction of the wire sections and passing one of the wire sections around the other so that the double loop configuration is made. This type of knot has been used in the cell pattern shown in FIGS. 1b and 1c, and it is well suited and preferred for cells of diamond shape. It appears that each rhomboid or diamond shaped cell includes four cell sides 8 and four cell junctions 6.

The wire or filament material used for the various wire frames in the devices according to the invention is preferably nitinol®, which has excellent elastic properties and can tolerate large deformations. Alternatively, stainless steel, titanium, copper alloys, tantalum or other biologically compatible materials capable of maintaining the expanded state inside the vessel, or mixtures of such materials may be used. If the device is a stent to be balloon-expanded at the positioning in the vessel, stainless steel may be just as suitable as nitinol®. It is also possible to use a synthetic material as the wire material, such as modified butadiene or another synthetic material with good resilient properties.

The cross-sectional area of the cell sides is chosen on the basis of the desired frame size, desired rigidity and the cell shape in the frame, a larger cross-sectional area being used at larger diameters, at a larger desired rigidity and/or at more open cells or lower cell number.

Figure 7C:
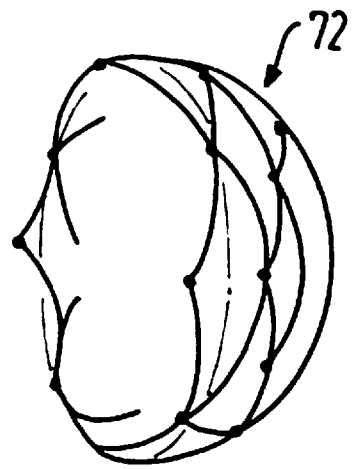
Figure 7A:
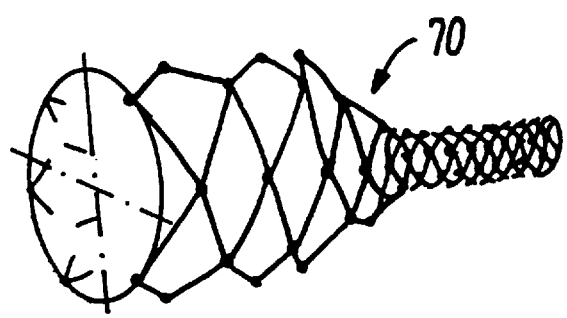
Figure 7B:
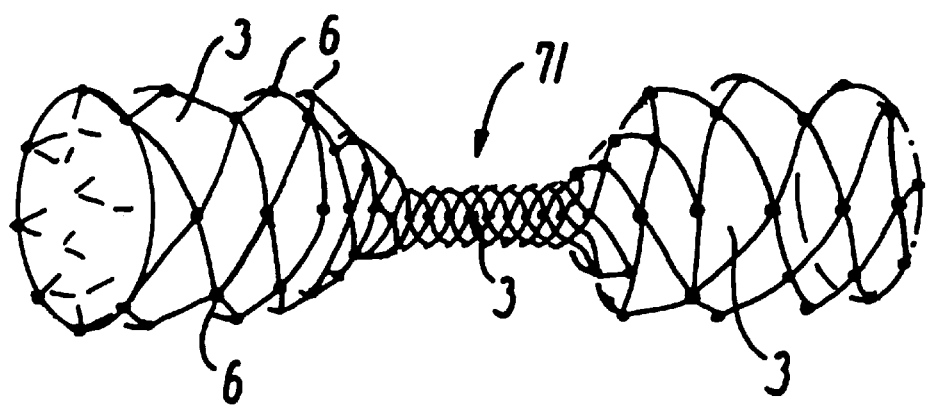

The tubular wire frame portions shown in FIGS. 1c, 2d and 3c may be used for stents or for the even diameter sections of the wire frames shown in FIGS. 7a and 7b.

When the wire frame is a stent for use in the Iliac, the stent may, for example, have a diameter of 8 mm, there may be four cells in each annular row, and the filament may, for example, be a nitinol® wire with a diameter of 0.16 mm. A corresponding stent can be used in bile ducts, the lumen of which is reduced by tumours or fibrosis. Stents may also be used for expanding the oesophagus in patients suffering from malignant dysphagia, for expanding the urinary tracts or other body vessels. A very important field of application is stents for expanding constrictions in blood vessels or for maintaining expanded vasoconstrictions, such as in hard stenoses. The below list mentions examples of applicable stent diameters, etc., for different applications.

| Field of application | Stent diameter |
| --- | --- |
| Arteries | |
| Coronary | 2–4 mm |
| Iliac | 6–12 mm |
| Femoral | 6–12 mm |
| Renal | 6–12 mm |
| Carotid | 6–12 mm |
| Aortic aneurism | 15–30 mm |
| Veins | |
| Vena cava | 12–30 mm |
| Vena subclavia | 12–30 mm |
| Arteriovenous shunt endoprosthesis | 6–14 mm |
| TIPS (by-pass in liver) | 10–12 mm |
| Urology | |
| Uretal | 4–7 mm |
| Urethral | 4–7 mm |
| Gastro-enterology | |
| Oesophageal | 18 mm at the middle |
| Biliary | 6–10 mm |
| Pancreatic | 2–3 mm |
| Thorax | |
| Bronchial | 15–20 mm |

The filament or wire diameter is adapted to the stent diameter, the cell sides being given less cross-sectional area at smaller stent diameters. The wire diameter may, for example, be in the interval of 0.06–0.40 mm.

It is possible to supplement the wire frame with a sheath of a suitably material, such as dacron®, PTFE or another biocompatible material. The use of such a graft on a wire frame is well-known in the art and needs no further description.

A second type of knot 10 is seen in FIG. 2a. For the sake of simplicity the separate wire sections are in the following designated with 4, 5 as in FIG. 1 and likewise the cell junctions are all designated with 6. In the various frame embodiments the cells are designated with separate numbers for separate cell configurations.

The knot 10 comprise two cell junctions 6, and at the one junction the two wire sections 4, 5 are passed one turn around each other and are bend to extend towards the other junction so that each wire section is looped once over and under the other wire section. Then the two wire sections are twisted at least one turn around each other, and at the other junction one of the wire sections is bent in the desired exit direction, which as shown may be approximately in parallel with its incoming direction to said one junction, and the other wire section is passed in a loop-shape one turn around the said one wire section to exit approximately in parallel with its own incoming direction to said one junction. The distance between the two junctions in a pair may be varied according to need, and if the distance is large the two wire sections may be twisted twice or thrice around each other between the two junctions.

The knot 10 may be used for cells 11 with a square configuration as shown in FIGS. 2b and 2d or for cells 12 with a polygonal configuration, as indicated in FIG. 2c. The latter has a more dense frame structure, which may be preferred in applications where tissue ingrowth is to be prevented. In frame areas where knot 10 is used each wire section has a wavy or omega-shaped run in the length direction of the frame, which has been indicated by a broken line in FIGS. 2b and 2c. The resulting wire frame 1' depicted in FIG. 2d may have a more or less open structure in dependency upon the chosen distance between each pair of cell junctions.

A third type 20 of cell junction shown in FIG. 3a is also applicable in connection with wire frames having rhomboid cells 3. At each cell junction 6 the two wire sections are twisted one turn around each other about a twist axis directed in the circumferential direction B of the tubular wire frame. Despite this simple type of winding the cells remain stable to radial compression because the cells are rhomboid and the twist axis is circumferentially directed. If required the wire sections may be twisted tore than one turn about each other at each cell junction. The resulting configuration of the wire frame 1" appears from FIG. 3c. Here each wire section has a stepped helical run through the wire frame section as indicated by the broken line in FIG. 3b.

A fourth type of knot 30 is seen in FIG. 4. At the cell junction the two wire sections 4, 5 are twisted one turn about each other about a twist axis 31 extending in a first direction and then the wire sections are bent in direction of a second twist axis 32 extending at an angle, preferably at approximately 90° to said first direction, and are twisted at least one turn about each other. This type of knot is particularly useful in respect of stents.

In the following, further examples of devices according to the invention and having varied geometrical shapes are described.

Figure 5A:
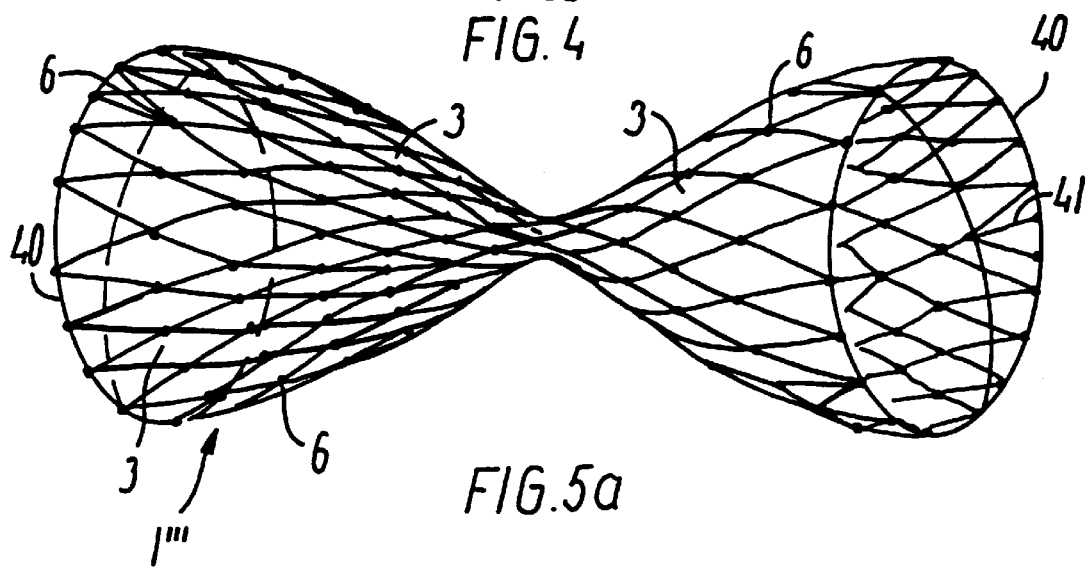

An intravenous filter shown in FIG. 5a comprises two coaxial interconnected bodies of revolution and each defined by wire sections forming cells 6 of a general rhombic shape over at least part of the surface of the body of revolution.

The body of revolution may assume a more or less pronounced parabolic shape.

For the purpose of reliably fixing the filter at a site of installation in a vein such as the lower caval vein anchoring members may be provided along the end rims 40 of the frame body 1'''.

As a special feature the filter may be provided with wire members 41 extending diametrically across the base of one or both of the bodies of revolution and being secured to one another at the centre of the base to function as extraction members engageable by a hook-shaped trapping wire introduced into the vein by means of a retraction catheter, not shown.

Due to the cellular surface of each of the bodies of revolution and the geometrical shape thereof as explained above, the entire filter composed of the two bodies of revolution may be stretched in the direction of its axis and arranged in the distal end of a hollow radioopaque introduction catheter of a small external diameter, e.g 2.5 mm, which may be introduced percutaneously into the vascular system of a patient through a paracentetic puncture in a femoral or subclavian vein.

Such a small diameter introduction catheter will cause minimum traumatization of the walls of the vein through which the catheter with the filter is introduced.

At the desired site of implantation, such as in the lower caval vein, the filter is ejected from the introduction catheter by means of a pushing member slidably arranged inside the catheter and, by dimensioning the diameter of the base of each of the bodies of revolution to be larger than the diameter of the vein or other vessel, reliable localization of the filter may be obtained also in case of temporary implantation where anchoring members are not used. For permanent installations an even more reliable localization may be obtained by means of said anchoring members.

In the illustrated embodiment of the filter with two slightly parabolic bodies of revolution one of these bodies will form an active filter part having its apex oriented downstream with respect to the blood flow whereby thrombotic masses will be collected at the apex and thus in the center of the lumen of the vein in which the filter is arranged. In the peripheral parts of the lumen a substantially free flow of blood will be ensured. Thereby, the risk of obturation of the vein lumen by thrombotic masses will be significantly reduced. The cells 6 are preferably goemetrically locked at the cell junctions by means of knots 7 of the first type.

The filter may also be made of a single body of revolution of a general shape as outlined above.

Figure 6A:
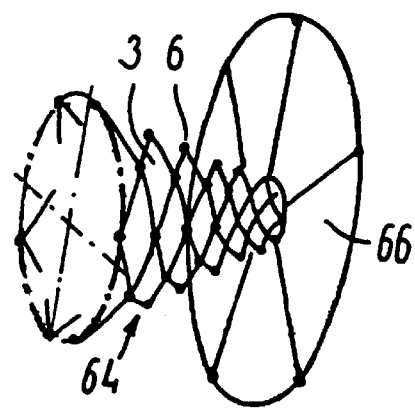
Figure 6B:
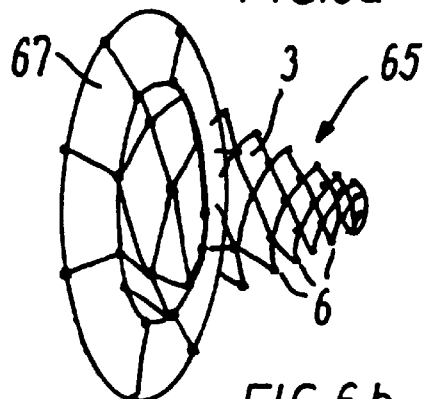
Figure 6C:
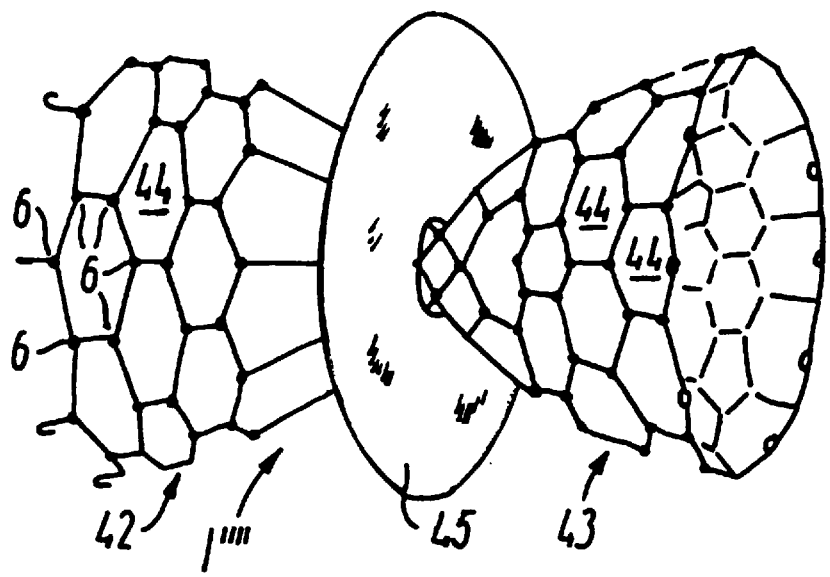

In FIG. 6c another embodiment of the implantation device of the invention is illustrated which is intended to function as a vessel occlusion device. Also in this embodiment the device includes a wire frame 1'''' composed of two bodies of revolution 42, 43 each of which has a general shape as described above and is defined by wire sections forming substantially hexagonal cells 44 over at least a part of the surface of the body of revolution. The cells 44 are preferably goemetrically locked at the cell junctions by means of knots 10 of the second type and/or knots 30 of the fourth type.

As described above for the filter embodiment of FIG. 5a the occluder embodiment in FIG. 6c may be easily arranged in the distal end of an introduction catheter, not shown, having a fairly small external diameter such as 2.5 mm and may be percutaneously introduced through the venous system or a puncture hole in a vessel segment. After introduction the occlusion device is ejected from the catheter and may completely obturate a vessel lumen due to an elastic membrane 45 which is reliably retained at the site of implantation by the self-expansion of the two bodies of revolution 42 and 43 assisted by the pressure gradient from the blood the flow of which is instantly blocked by the occlusion of the vessel.

Due to its flexibility and the general shape of the bodies of the revolution as well as the cellular surface made up of the wire sections the occlusion device is very flexible and suitable for introduction by means of an equally flexible conveying system whereby the risk of traumatization may be kept very low and the universality of the occlusion device for implantation in vessels of various diameters and geometry is ensured.

Instead of being joined together at their apices the two bodies of revolution may have their apices somewhat separated and displaceably connected by a flexible axially extending wire member to which the elastic blood impermeable membrane 45 is fixed. With this modification the occlusion device may be suitable for closing of a socalled ASD-defect i.e. a defect in the atrial septum between the right and left atria.

Figure 6E:
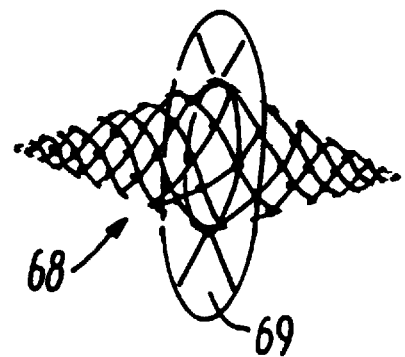
Figure 6D:
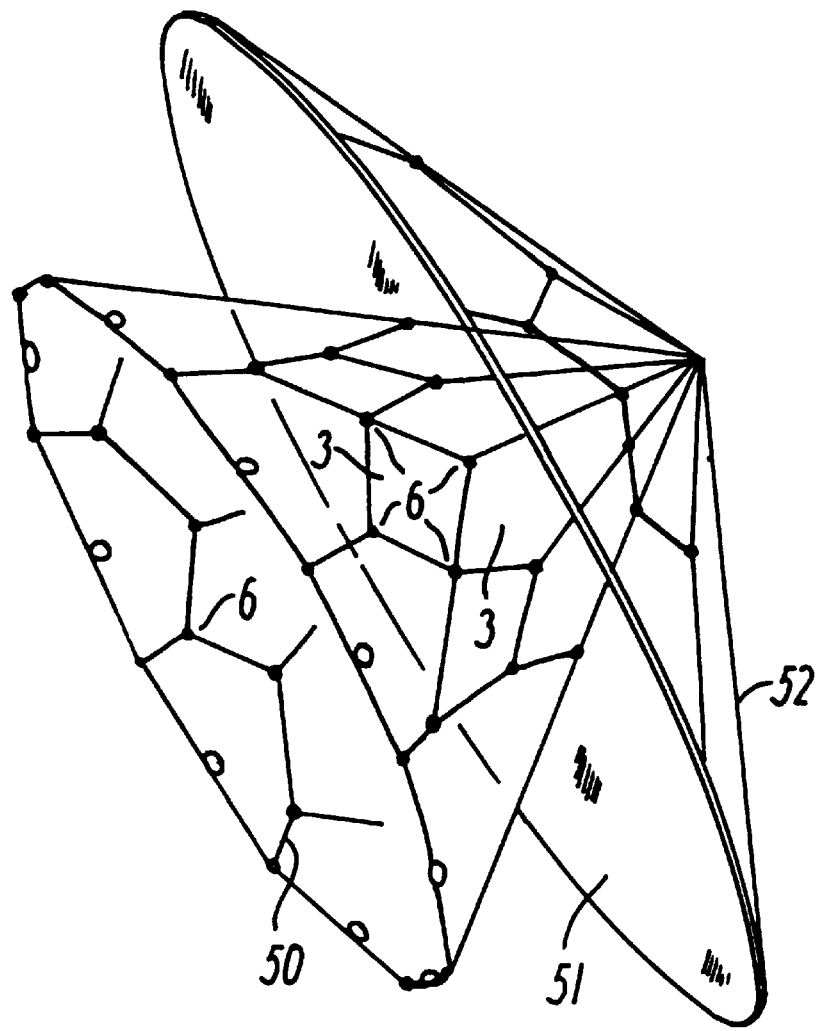

FIG. 6d shows a different embodiment of an occlusion device specially intended for curing the fatal condition known as Patent Ductus Arteriosis (PDA) caused by a duct or flow passage between the pulmonary artery and the aorta. In this embodiment, the device comprises only a single body of revolution So which as shown may be of a generally conical shape the apical end of which is connected through a flexible link of wire sections with the elastic blood impermeable membrane 51 which in this case may be supported on its external side by an umbrella-like wire frame structure 52. In this embodiment the cells of the wire frame are of mixed configurations, such as pentagonal cells and rhomboid cells.

Figure 5B:
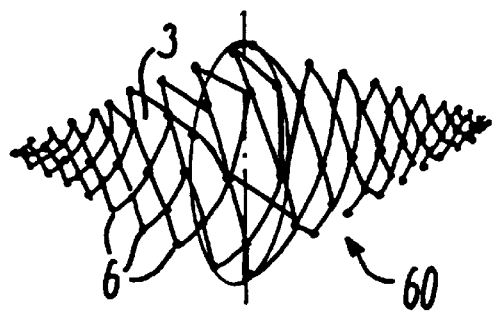
Figure 5C:
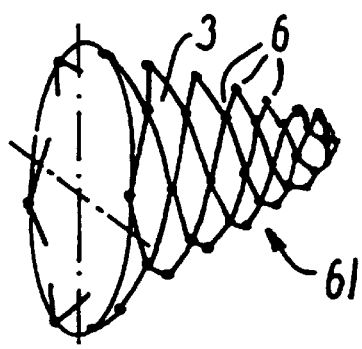
Figure 5D:
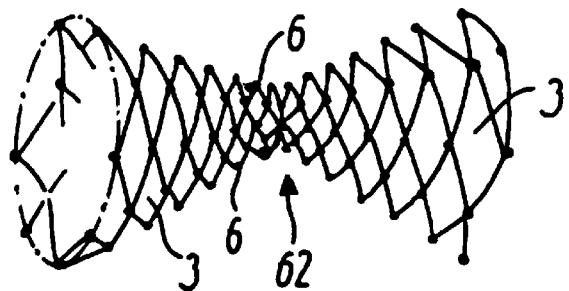
Figure 5E:
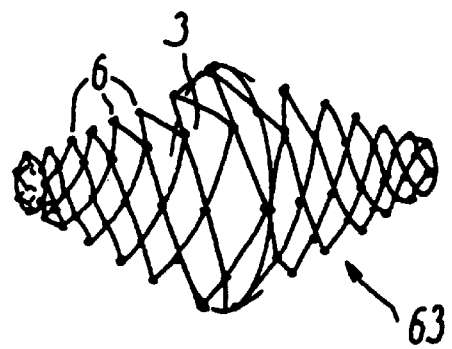

Examples of other wire frame types using rhomboid cells and knots of the types e.g. 7 or 20 may be briefly mentioned. FIG. 5b shows a variant of the device in the form of a wire frame 60 having a double cone with connected bases. FIG. 5c shows a wire frame 61 shaped as a single truncated cone. FIG. 5d and 5e show wire frames 62, 63 including two truncated cones. FIG. 6a and 6b show wire frames 64, 65 with an impermeable membrane 66, 67 secured to its apex and base, respectively. FIG. 6e shows a wire frame 68 shaped as a double cone with connected bases and with an impermeable membrane 69 positioned between the bases. FIG. 7a shows a wire frame 70 shaped as a semi-bar bell. FIG. 7b shows a wire frame 71 shaped as a bar bell, and lastly FIG. 7c shows a wire frame 72 shaped as a hemisphere.

The various wire frames may as indicated above be placed inside an introducer catheter in a radially compressed state, either by being extended by an axial pull at both ends of the wire frame or by being subjected to a radially inwardly directed pressure, e.g. by being pushed through a cone shaped loading sheet. When the device has been introduced to the desired lumen site, it is pushed or pulled out of the introducer catheter and due to the cell structure and the geometrical locking at the cell junctions the wire frame self-expands to approximately its initial shape.

Whereas various embodiments of the implantable device of the invention have been described hereinbefore these examples and the medical applications associated therewith should not be considered exhaustive. The invention opens for a wide range of modifications and further developments of wire frame configurations and knot types in devices for treatment of a diversity of defects in the human vascular system within the scope of the following claims.

What is claimed is:

1. A device for implantation in a vessel or hollow organ lumen in a human or animal body, the device comprising a wire frame with a plurality of interconnected cells made of at least two separate wire sections which are intercrossing at cell junctions and form closed cells, wherein at the cell junctions, the wires are knotted to form a geometrical locking of the cells so that wire-shaped cell sides in respective cells are locked at the cell junctions in a manner preventing relative movement with respect to each other when the wire frame is in its expanded condition and subjected to pressure acting radially inwardly.

2. A device according to claim 1, wherein the wire frame includes rhomboid cells each having four cell sides and four cell junctions positioned at apices of the cell.

3. A device according to claim 1, wherein the wire frame includes square cells each having four cell sides and four cell junctions.

4. A device according to claim 1, wherein the wire frame includes polygonal cells each having more than four cell sides and a corresponding number of cell junctions.

5. A device according to claim 1, wherein the wire frame includes cell junctions where at least two wire sections are loop-shaped, and wherein the two cell sides carrying the loop on one of the wire sections pass through the loop of the other wire section, whereby said junctions preferably are square knot-like.

6. A device according to claim 2, wherein the wire frame includes cell junctions where at least two wire sections are loop-shaped, and wherein the two cell sides carrying the loop on one of the wire sections pass through the loop of the other wire section, whereby said junctions preferably are square knot-like.

7. A device according to claim 3, wherein the wire frame includes cell junctions where at least two wire sections are loop-shaped, and wherein the two cell sides carrying the loop on one of the wire sections pass through the loop of the other wire section, whereby said junctions preferably are square knot-like.

8. A device according to claim 4, wherein the wire frame includes cell junctions where at least two wire sections are loop-shaped, and wherein the two cell sides carrying the loop on one of the wire sections pass through the loop of the other wire section, whereby said junctions preferably are square knot-like.

9. A device according to claim 1, wherein the wire frame includes pairs of cell junctions where one wire section is looped once over and under an other wire section, wherein at each cell junction and between the junctions in a pair the wire sections are twisted at least one turn about each other.

10. A device according to claim 2, wherein the wire frame includes pairs of cell junctions where one wire section is looped once over and under an other wire section, wherein at each cell junction and between the junctions in a pair the wire sections are twisted at least one turn about each other.

11. A device according to claim 3, wherein the wire frame includes pairs of cell junctions where one wire section is looped once over and under an other wire section, wherein at each cell junction and between the junctions in a pair the wire sections are twisted at least one turn about each other.

12. A device according to claim 4, wherein the wire frame includes pairs of cell junctions where one wire section is looped once over and under an other wire section, wherein at each cell junction and between the junctions in a pair the wire sections are twisted at least one turn about each other.

13. A device according to claim 1, wherein the wire frame includes cell junctions where two wire sections are twisted one turn about each other about a twist axis extending in a first direction and at least one turn about each other about a second twist axis extending at an angle to said first direction.

14. A device according to claim 2, wherein the wire frame includes cell junctions where two wire sections are twisted one turn about each other about a twist axis extending in a first direction and at least one turn about each other about a second twist axis extending at an angle to said first direction.

15. A device according to claim 3, wherein the wire frame includes cell junctions where two wire sections are twisted one turn about each other about a twist axis extending in a first direction and at least one turn about each other about a second twist axis extending at an angle to said first direction.

16. A device according to claim 4, wherein the wire frame includes cell junctions where two wire sections are twisted one turn about each other about a twist axis extending in a first direction and at least one turn about each other about a second twist axis extending at an angle to said first direction.

17. A device according to claim 5, wherein the wire frame includes cell junctions where two wire sections are twisted one turn about each other about a twist axis extending in a first direction and at least one turn about each other about a second twist axis extending at an angle to said first direction.

18. A device according to claim 9, wherein the wire frame includes cell junctions where two wire sections are twisted one turn about each other about a twist axis extending in a first direction and at least one turn about each other about a second twist axis extending at an angle to said first direction.

19. A device according to claim 13, wherein the wire frame includes a tubular portion with a mainly even diameter, and wherein said first direction extends approximately in a circumferential direction of said tubular portion and said second twist axis extends approximately in a longitudinal direction of said tubular portion.

20. A device according to claim 2, wherein the wire frame includes a tubular portion with cell junctions where two wire sections are twisted at least one turn about each other about a twist axis extending approximately in a circumferential direction of said tubular portion.

* * * * *